United States Patent [19]

Faarup et al.

[11] Patent Number: 5,646,146

[45] Date of Patent: Jul. 8, 1997

[54] HETEROCYCLIC COMPOUNDS AND THEIR PREPARATION AND USE

[75] Inventors: Peter Faarup; Palle Jakobsen, both of Værløse; Anker Steen Jørgensen, København; Henrik Klitgaard, Birkerød, all of Denmark

[73] Assignee: Novo Nordisk A/S, Bagsvaerd, Denmark

[21] Appl. No.: 450,836

[22] Filed: May 25, 1995

Related U.S. Application Data

[62] Division of Ser. No. 189,524, Jan. 31, 1994, Pat. No. 5,468,748.

[30] Foreign Application Priority Data

Feb. 2, 1993 [DK] Denmark ................... 0122/93

[51] Int. Cl.$^6$ .............. A61K 31/495; A61K 31/675; C07D 241/38; C07F 9/6509
[52] U.S. Cl. ............ 514/250; 514/232.8; 514/80; 544/115; 544/337; 544/344
[58] Field of Search ............ 514/80, 232.8, 514/250; 544/115, 337, 344

[56] References Cited

U.S. PATENT DOCUMENTS

| | | | |
|---|---|---|---|
| 4,889,855 | 12/1989 | Jacobsen et al. | 514/250 |
| 4,912,108 | 3/1990 | Jacobsen et al. | 514/250 |
| 5,026,704 | 6/1991 | Honore et al. | 514/250 |
| 5,081,123 | 1/1992 | Honore et al. | 514/250 |
| 5,153,195 | 10/1992 | Honore et al. | 514/250 |
| 5,182,279 | 1/1993 | Jorgensen et al. | 514/250 |

FOREIGN PATENT DOCUMENTS

| | | |
|---|---|---|
| 0 511 152 A2 | 10/1992 | European Pat. Off. . |
| 9526342 | 10/1995 | WIPO . |

OTHER PUBLICATIONS

Bergel et al, "Journal of Chemical Society", 1964, University College, (London), pp. 3973–3981.

A.W. Johnson et al, "Journal of Chemical Society", 1960, University College, (London), pp. 3412–3413.

*Primary Examiner*—Emily Bernhardt
*Attorney, Agent, or Firm*—Steve T. Zelson, Esq.; Elias J. Lambiris, Esq.

[57] ABSTRACT

The present invention relates to 9H-indeno[1,2-b]pyrazin-3(4H)-ones and 9H-indeno[1,2-b]pyrazine-2,3(1H,4H)-diones or tautomeric forms thereof which are useful in treating neurological and psychiatric diseases based on the antagonism of the glycine binding site on the NMDA receptor complex.

29 Claims, No Drawings

HETEROCYCLIC COMPOUNDS AND THEIR PREPARATION AND USE

This application is a divisional of application Ser. No. 08/189,524, filed Jan. 31, 1994 now U.S. Pat. No. 5,468,748, which is incorporated herein by reference.

The present invention relates to therapeutically active 9H-indeno[1,2-b]-pyrazin-3(4H)-one and 9H-indeno[1,2-b]pyrazine-2,3(1H,4H)-dione derivatives or tautomeric forms thereof, a method of preparing the same, pharmaceutical compositions comprising the compounds, and a method of treating therewith.

Interaction with glutamic acid mediated neurotransmission is considered a useful approach in the treatment of neurological and psychiatric diseases. Thus, known antagonists of excitatory amino acids have shown potent antiepileptic and muscle relaxant properties (A. Jones et al., Neurosci. Lett. 53, 321 (1985)) as well as anxiolytic activity (D. A. Bennett et al., Life Sci. 39, 2355 (1986)).

It has been suggested that accumulation of extracellular excitatory and neurotoxic amino acids, followed by hyperstimulation of neurons, may explain the neuronal degenerations seen in neurological diseases as Huntingtons chorea, Parkinsonism, epilepsy, senile dementia, and deficiencies of mental and motoric performance seen after conditions of brain ischemia, anoxia and hypoglycemia (E. G. McGeer et al., Nature, 263, 517 (1976) and R. Simon et al., Science, 226, 850 (1984)).

Excitatory amino acids exert their actions via specific receptors located postsynaptically or presynaptically. Such receptors are at present conveniently subdivided into four groups based on electrophysiological and neuro-chemical evidence: AMPA, metabotropic, kainate and NMDA receptors. L-glutamic acid and aspartic acid probably activate all the above types of excitatory amino acid receptors and possibly other types as well.

It was recently found that glycine was essential for NMDA receptor agonist induced responses in cultured neurons (J. W. Johnson et al., Nature 325, 529 (1987)). In contrast to glycine activated chloride conductance in spinal cord neurons, this response was insensitive to strychnine (D. W. Bonhaus et al., European J. Pharmacol. 142, 489 (1987)).

Glycine is believed to potentiate NMDA action through a modulatory site allosterically coupled to the NMDA ionophore complex (T. Honoré et al., European J. Pharmacol. 172, 239 (1989)). D-serine and D-alanine exert a strong agonist activity on this site (J. B. Monaban et al., J. Neurochem. 53, 370 (1989)), whereas 1-amino-cyclopropanecarboxylate (P. Skolnick et al., Life Sci. 45, 1647 (1989), V. Nadler et al., European J. Pharmacol. 157, 115 (1988), R. Trullas et al., Pharmacol. Biochem. Behav., 34, 313 (1989)) and D-cycloserine (W. F. Hood et al., Neurosci. Lett. 98, 91 (1989)) act as partial agonists.

1-amino-cyclobutanecarboxylate (W. F. Hood et al., European J. Pharmacol. 161, 281 (1989)), 1-amino-cyclopentanecarboxylate (L. D. Snell et al., European J. Pharmacol. 151, 165 (1988)), 3-amino-1-hydroxy-2-pyrrolidone (HA-966) (E. J. Fletcher et al., European J. Pharmacol. 151, 161 (1988)), 5-chloro-indole-2-carboxylate (J. E. Huettner, Science 243, 1611 (1989)) and 6-cyano-7-nitroquinoxaline-2,3-dione (CNQX) (R. A. J. Lester et al., Mol. Pharmacol. 35, 565 (1989)) are all weak antagonists, whereas 7-chloro-kynurenic acid (7-Cl-Kyn) (R. Sircar et al., Brain Res. 504, 325 (1989)) and 6,7-dichloro-3-hydroxy-quinoxaline-2-carboxylate (M. Kessler et al., Brain Res. 489, 377 (1989)) are quite strong antagonists of glycine at the glycine site. However, all of the above reported compounds act nonselectively at this site in so far as they have higher or equal affinity for other targets.

We have now discovered novel 9H-indeno[1,2-b] pyrazin-3(4H)-one and 9H-indeno[1,2-b]pyrazine-2,3(1H, 4H)-dione derivatives which are potent and selective antagonists at the glycine binding site on the NMDA receptor complex.

The present invention accordingly provides compounds of formula (I) or tautomeric forms thereof selected from the group consisting of

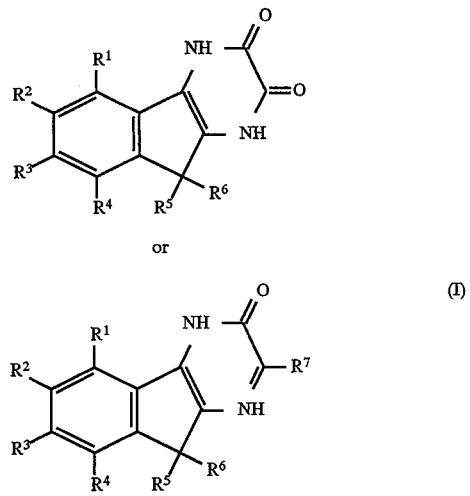

(I)

wherein $R^1$, $R^2$, $R^3$ and $R^4$ independently represent hydrogen, halogen, $C_{1-6}$-alkyl or $C_{1-6}$-alkoxy; and $R^5$ represents hydrogen, hydroxy, halogen, cyano, $C_{1-6}$-alkyl optionally substituted with hydroxy, $C_{1-6}$-alkoxy optionally substituted with one or two phenyl group(s) which phenyl group(s) is/are optionally substituted with halogen, $C_{1-6}$-(alkoxyalkoxy), $C_{1-6}$-thioalkyl optionally substituted with an amino group which amino group is optionally mono or disubstituted with $C_{1-6}$-alkyl, $C_{1-6}$-acyloxy, phosphono, $C_{1-6}$-alkoxy disubstituted phosphonyl or a 5 or 6 membered heterocyclic group containing one or two N or O atom(s) or a combination thereof which heterocyclic group is optionally substituted with $C_{1-6}$-alkyl which alkyl group is optionally substituted by hydroxy or which heterocyclic group is optionally substituted with one or two phenyl group(s) which phenyl group(s) is/are optionally substituted with methoxy; and $R^6$ represents hydrogen, $C_{1-6}$-alkyl or phenyl, or $R^5$ and $R^6$ together represent a carbonyl group, a hydroxyimino group or a benzyloxyimino group, or $R^5$ and $R^6$ together form a 5 or 6 membered heterocyclic group containing one or two N, O, S or S(O)z atom(s) or a combination thereof, wherein z is 1 or 2, which heterocyclic group is optionally substituted with one or two methyl group(s), hydroxymethyl, piperidinomethyl or (4-methyl-1-piperazinyl)methyl; and $R^7$ represents hydrogen, phenyl or —$CH_2OR^8$ wherein $R^8$ is hydrogen or benzyl, or a pharmaceutically acceptable salt thereof.

These salts include pharmaceutically acceptable acid addition salts, pharmaceutically acceptable metal salts or optionally alkylated ammonium salts, such as hydrochloric, hydrobromic, hydroodic, phosphoric, sulfuric, trifluoroacetic, trichloroacetic, oxalic, maleic, pyruvic, malonic, succinic, citric, mandelic, benzoic, cinnamic, methanesulfonic, ethane sulfonic, picric and the like, and include acids related to the pharmaceutically acceptable salts listed in Journal of Pharmaceutical Science, 66, 2 (1977) and incorporated herein by reference, or lithium, sodium, potassium, magnesium and the like.

The invention also relates to methods of preparing the novel 9H-indeno[1,2-b]pyrazin-3(4H)-one and 9H-indeno [1,2-b]pyrazine-2,3(1H,4H)-dione derivatives. These methods involves reacting commercially available intermediates or intermediates prepared by standard procedures of formula (II)

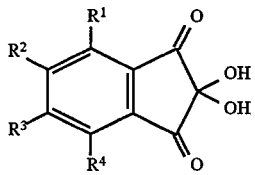

(II)

wherein $R^1$, $R^2$, $R^3$ and $R^4$ have the meanings as defined for formula (I) with a compound of formula (III)

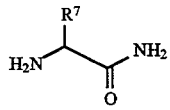

(III)

wherein $R^7$ has the meaning as defined for formula (I), to form a compound of formula (IV)

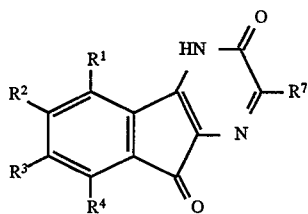

(IV)

wherein $R^1$, $R^2$, $R^3$, $R^4$ and $R^7$ have the meanings as defined for formula (I).

Oxidizing a compound of formula (IV) wherein $R^1$, $R^2$, $R^3$ and $R^4$ have the meanings as defined for formula (I) and $R^7$ is hydrogen with, e.g. hydrogen peroxide, in a mixture of acetic acid and acetic anhydride to form a compound of formula (V)

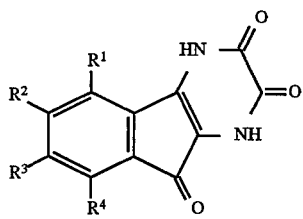

(V)

wherein $R^1$, $R^2$, $R^3$ and $R^4$ have the meanings set forth above.

Reacting a compound of formula (V) with hydroxylamine or O-benzylhydroxylamine to form a compound of formula (VI)

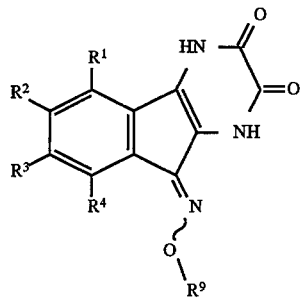

(VI)

wherein $R^1$, $R^2$, $R^3$ and $R^4$ have the meanings set forth above and $R^9$ represents hydrogen or benzyl.

Reducing a compound of formula (V) with, e.g. sodium borohydride, to form a compound of formula (VII)

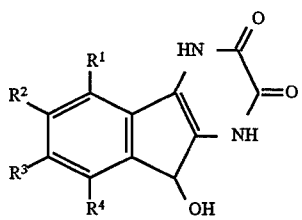

(VII)

wherein $R^1$, $R^2$, $R^3$ and $R^4$ have the meanings set forth above.

Reacting a compound of formula (VII) with a halogenating agent, e.g. thionyl chloride or thionyl bromide, to form a compound of formula (VIII)

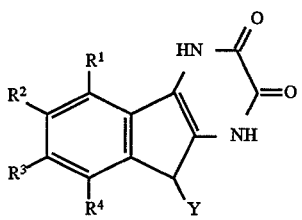

(VIII)

wherein $R^1$, $R^2$, $R^3$ and $R^4$ have the meanings set forth above and Y is halogen.

Reacting a compound of formula (VIII) with $R^{10}$—COOH, wherein $R^{10}$ is alkyl, to form a compound of formula (IX)

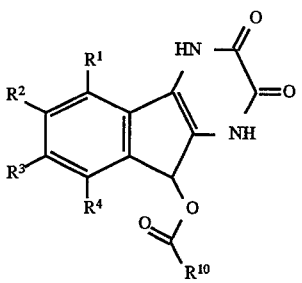

(IX)

wherein $R^1$, $R^2$, $R^3$, $R^4$ and $R^{10}$ have the meanings set forth above.

Reacting a compound of formula (VIII) or a compound of formula (VII) with an alcohol $R^{11}$—OH, wherein $R^{11}$ represents alkyl optionally substituted with one or two phenyl group(s) which phenyl group(s) is/are optionally substituted with halogen or alkoxyalkyl, e.g. ethyl, 3,3-diphenylpropyl, 2,2-(4-chlorophenyl)ethyl or 2-methoxyethyl, to form a compound of formula (X)

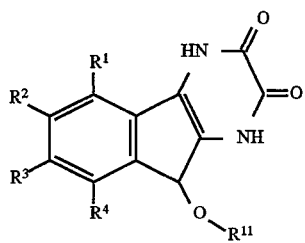

wherein $R^1$, $R^2$, $R^3$, $R^4$ and $R^{11}$ have the meanings set forth above.

Reacting a compound of formula (IV) with 1,3 or 1,2-diols, which may be substituted with one or two lower alkyl group(s) in an inert solvent such as benzene or toluene in the presence of an acid catalyst to form a compound of formula (XI) or (XII)

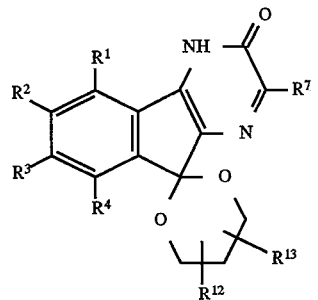

or

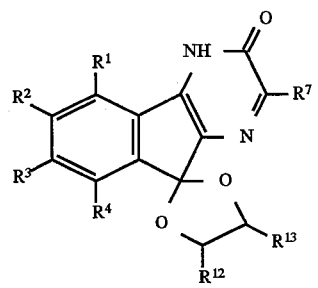

wherein $R^1$, $R^2$, $R^3$, $R^4$ and $R^7$ have the meanings as defined for formula (I) and $R^{12}$ and $R^{13}$ represent an alkyl group, e.g. methyl.

Oxidizing a compound of formula (XII) wherein $R^7$ is hydrogen with, e.g. hydrogen peroxide, in a mixture of acetic acid and acetic anhydride to form a compound of formula (XIII)

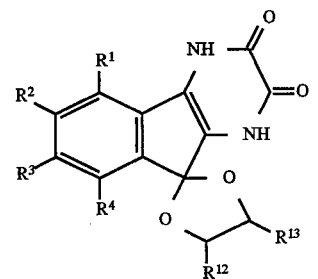

wherein $R^1$, $R^2$, $R^3$, $R^4$, $R^{12}$ and $R^{13}$ have the meanings as defined for formula (XII).

Reacting a compound of formula (VIII) with an amine

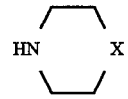

wherein X is oxygen or N—$R^{14}$, wherein $R^{14}$ represents hydrogen or an alkyl group, e.g. methyl, or a substituted alkyl group, e.g. 2-hydroxyethyl, diphenylmethyl or a phenyl group which is optionally substituted with methoxy, e.g. 2-methoxyphenyl, in a suitable solvent such as tetrahydrofuran to form a compound of formula (XIV)

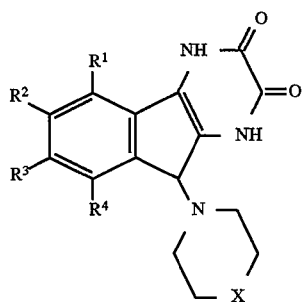

wherein $R^1$, $R^2$, $R^3$ and $R^4$ have the meanings as defined for formula (I) and X and N—$R^{14}$ have the meanings defined above.

Reacting a compound of formula (VIII) with an alkylphosphite to form a compound of formula (XV)

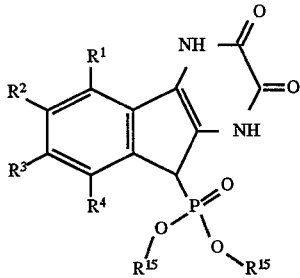

wherein $R^1$, $R^2$, $R^3$ and $R^4$ have the meanings set forth above and $R^{15}$ is methyl or ethyl.

Reacting a compound of formula (XV) with bromotrimethylsilane in acetonitrile to form a compound of formula (XVI)

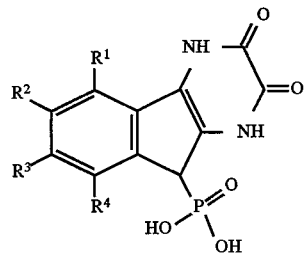

wherein $R^1$, $R^2$, $R^3$ and $R^4$ have the meanings set forth above.

Reacting a compound of formula (V) with 1,3 or 1,2-dithiols which may be substituted with one or two lower alkyl group(s) in an inert solvent such as toluene in the presence of boron trifluoride etherate to form a compound of formula (XVII) or (XVIII)

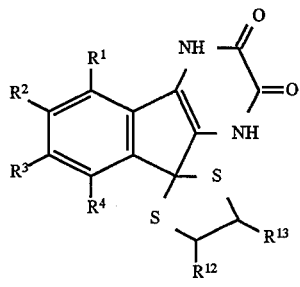

(XVII)

or

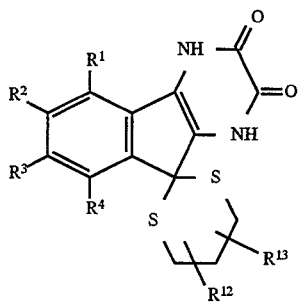

(XVIII)

wherein $R^1$, $R^2$, $R^3$, $R^4$, $R^{12}$ and $R^{13}$ have the meanings set forth above.

Oxidizing a compound of formula (XVII) with, e.g. hydrogen peroxide, in a mixture of acetic acid and acetic anhydride to form a compound of formula (XIX)

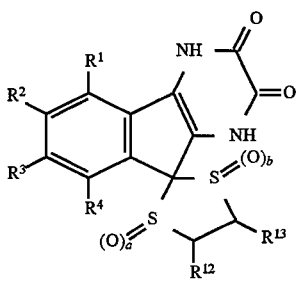

(XIX)

wherein $R^1$, $R^2$, $R^3$, $R^4$, $R^{12}$ and $R^{13}$ have the meanings set forth above and a and b independently are 0, 1 or 2, provided that a and b are not 0 at the same time.

Reacting a compound of formula (VII) with alkylthiol or 2-aminoalkylthiol optionally substituted in the amino group with lower alkyl in acetic acid in the presence of boron trifluoride etherate to form a compound of formula (XX)

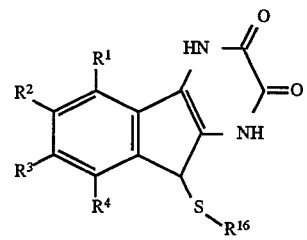

(XX)

wherein $R^1$, $R^2$, $R^3$ and $R^4$ have the meanings set forth above and $R^{16}$ is thioalkyl optionally substituted with an amino group which amino group is optionally mono or disubstituted with alkyl.

Silylating a compound of formula (IV) with, e.g. trimethylsilyl chloride and triethylamine, in a suitable solvent such as tetrahydrofuran and thereafter, reacting with alkyl or phenylmagnesium bromide and subsequent hydrolysis to form a compound of formula (XXI)

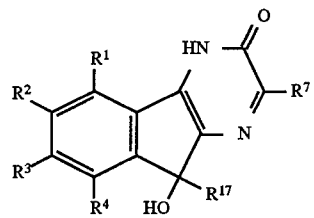

(XXI)

wherein $R^1$, $R^2$, $R^3$, $R^4$ and $R^7$ have the meanings as defined for formula (I) and $R^{17}$ is alkyl or phenyl.

Reacting a compound of formula (XXI) with a mixture of $R^{10}$—COOH, $(R^{10}$—$CO)_2O$ and hydrogen peroxide to form a compound of formula (XXII)

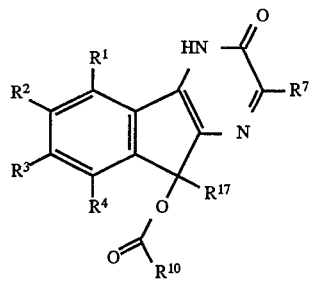

(XXII)

wherein $R^1$, $R^2$, $R^3$, $R^4$ and $R^7$ have the meanings as defined for formula (I) and $R^{10}$ and $R^{17}$ have the meanings set forth above.

Silylating a compound of formula (V) with, e.g. trimethylsilyl chloride and triethylamine, in a suitable solvent such as tetrahydrofuran and thereafter reacting with alkyl or phenylmagnesium bromide and subsequent hydrolysis to form a compound of formula (XXIII)

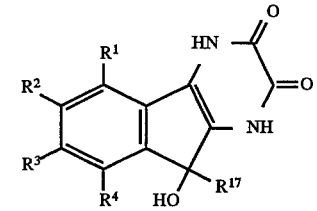

(XXIII)

wherein $R^1$, $R^2$, $R^3$ and $R^4$ have the meanings as defined for formula (I) and $R^{17}$ has the meaning set forth above.

Reacting a compound of formula (XXIII) with an alcohol $R^{18}$—OH wherein $R^{18}$ is alkyl to form a compound of formula (XXIV)

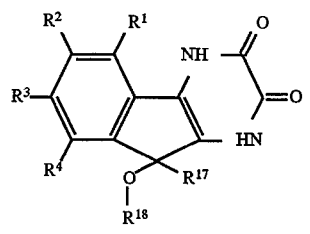

(XXIV)

wherein $R^1$, $R^2$, $R^3$ and $R^4$ have the meanings as defined for formula (I) and $R^{17}$ and $R^{18}$ have the meanings set forth above.

The compounds according to the invention were tested as regards the affinity for one or more of the different types of excitatory amino acid receptors and studied in simple radioligand binding experiments. In essence, the method involves incubation of a particular selected radio-labelled ligand and the particular specific substance to be investigated with brain homogenates which contain the receptor. Measurement of receptor occupancy is made by determination of the specific radioactivity bound to the homogenate.

It has now been found that the heterocyclic compounds of the invention have affinity for the glycine site of the NMDA receptor complex and are antagonists in connection with this type of receptors. This will make them useful in the treatment of any of the numerous indications caused by hyperactivity of excitatory amino acids.

The glycine site binding activity of these compounds of the present invention can be illustrated by determining their capability for displacing radioactively labelled glycine from the glycine site.

The displacement activity of the compounds may be shown by determining the $IC_{50}$ value which represents the concentration (µM) which causes a displacement of 50% of the specific binding of [$^3$H]-glycine.

In summary, the influence of glutamic acid analogues on secondary effects of glutamate receptor interactions, such as on ligand-gated channel opening and G-protein mediated signal transduction, may be studied in vitro using brain slices, brain homogenates or clonal lines expressing glutamate receptor subtypes. Such experiments will provide information as to the efficacies (agonist/antagonist) of the test substances.

The glycine antagonistic properties of the compounds are demonstrated by their capability to counteract convulsions induced by i.c.v. infusion of NMDA. The glycine antagonists are co-infused with NMDA and their anti-convulsive effect is measured by determining a) the $TV_{50}$ value which represents the dose (µg/kg) of the glycine antagonist that has to be infused per minute in order to increase time to onset of clonic seizures by 50%, b) the $ED_{50}$ value which represents the dose (µg/kg) of the glycine antagonist that has to be infused per minute in order to protect 50% of the animals against clonic seizures for 150 seconds after the start of i.c.v. infusion.

In vitro [$^3$H]-Glycine Binding to Rat Brain Membranes (Test 1)

The membrane preparation and assay of specific [$^3$H]-glycine binding is based upon methodology described by Haring et al. (1991) J. Neurochem. 57, 323–332 and Yoneda et al. (1991) J. Neurochem. 55, 237–244.

All steps are performed at 4° C. Buffers are prepared fresh each week from distilled, deionized water and filtered through sterile 0.2 µm membranes to eliminate artifacts due to microbial contamination. Crude synaptic ($P_2$) membranes are prepared from rat forebrains freshly dissected from male Wistar rats and washed 4 times with low ionic strength buffer. On the day of the assay these preparations are additionally washed with buffer containing a low concentration (0.08% g/g) of Triton X-100, and then twice more in the absence of this detergent. The procedure is aimed at the disruption of synaptic membrane vesicles and removal of endogenous amino acids.

Specific radioligand binding is measured by incubating membranes (400–600 µg/ml of protein) with 50 nM [$^3$H]-glycine in the presence or absence of 1 mM of unlabelled glycine at 4° C. for 30 min. Free and bound ligand are separated by centrifugation. Each pellet is rinsed 2× and bound radioactivity measured by liquid scintillation counting. Test substances are substituted for Unlabelled glycine in the assay.

Convulsions induced by i.c.v. infusion of NMDA
(Test 2 & 3)

58.84 µg/ml (1 nmol in 2.5 µl) of NMDA (Sigma) dissolved in 0.9% NaCl is co-infused i.c.v. with a glycine antagonist at a speed of 5 µl/min. Infusion is performed through a cannula placed 1 mm posterior and 1 mm lateral to the Bregma point. The cannula is injected 4.3 mm into the skull of male NMRI mice weighing 25 g (range 23–27 g). Placement and length of the cannula into the skull is fixed by a plate positioned 4.3 mm from the point of the cannula. The infusion is stopped after the appearance of clonic seizures in all extremities or 150 seconds after the start time of the infusion. At least 5 doses of each glycine antagonist are tested using 8 mice per dose.

Test results obtained by testing some compounds of the present invention will appear from the following Table 1.

TABLE 1

| Compound of Example | Test 1 $IC_{50}$ µM | Test 2 $TV_{50}$ (µg/kg) | Test 3 $ED_{50}$ (µg/kg) |
|---|---|---|---|
| 2 | 0.92 | 44 | 170 |
| 6 | 3.7 | — | — |
| 11 | 0.92 | 5.0 | — |
| 18 | 0.15 | 4.5 | 7.0 |

The compounds of the invention, together with a conventional adjuvant, carrier, or diluent, and if desired in the form of a pharmaceutically acceptable salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective central nervous system ailment alleviating amount of the active ingredient commensurate with the intended daily dosage range to be employed. Tablets containing one (1) to two hundred (200) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or oral application which do not deleteriously react with the active compound.

Examples of such carriers are water, salt solutions, alcohols, polyethylene glycols, polyhydroxyethoxylated castor oil, gelatin, lactose, amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compound.

For parenteral application, particularly suitable are injectable solutions or suspensions, preferably aqueous solutions with the active compound dissolved in polyhydroxylated castor oil.

Ampoules are convenient unit dosage forms.

For oral application, particularly suitable are tablets, dragees, or capsules having talc and/or a carbohydrate carrier or binder or the like, the carrier preferably being lactose and/or corn starch and/or potato starch. A syrup, elixir or like can be used when a sweetened vehicle can be employed. Generally, as to broader ranges, the compounds of the invention are dispensed in unit dosage form comprising 0.05–100 mg in a pharmaceutically acceptable carrier per unit dosage.

A typical tablet which may be prepared by conventional tabletting techniques contains:

| Active compound | 2.0 mg |
|---|---|
| Lactosum | 67.8 mg Ph.Eur. |
| Avicel ® | 31.4 mg |
| Amberlite ® IRP 88 | 1.0 mg |
| Magnesii stearas | 0.25 mg Ph.Eur. |

Due to their high degree of effect as glycine antagonists, the compounds of the invention are extremely useful in the treatment of central nervous system ailments or disorders, when administered in an amount effective for the alleviation, amelioration, or elimination thereof. The important CNS activity of the compounds of the invention includes both anticonvulsant, hypnotic, nootropic, anxiolytic and antipsychotic activities along with a low toxicity, together presenting a most favourable therapeutic index. The compounds of the invention may accordingly be administered to a subject, e.g. a living mammal body, including a human, in need of the same for the treatment, alleviation, amelioration, or elimination of an indication, associated with the central nervous system and the so-called NMDA receptors, which requires such psychopharmaceutical treatment, e.g. especially convulsion, anxiety, epilepsy and ischemia, if desired in the form of a pharmaceutically acceptable salt thereof, ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective psychopharmaceutical central nervous system ailment alleviating amount, e.g. an anticonvulsant and/or anxiolytic amount, and in any event an amount which is effective for the alleviation of such a central nervous system ailment due to their NMDA receptor affinity. Suitable dosage ranges are 1–200 milligrams daily, depending as usual upon the exact mode of administration, form in which administered, the indication toward which the administration is directed, the subject involved and the body weight of the subject involved, and the preference and experience of the physician or veterinarian in charge.

The route of administration may be any route, which effectively transports the active compound to the appropriate or desired site of action, such as oral or parenteral e.g. rectal, transdermal, subcutaneous, intravenous, intramuscular or intranasal, the oral route being preferred.

The invention will now be described in further detail with reference to the following examples.

EXAMPLE 1

9H-Indeno[1,2-b]pyrazine-3,9(4H)-dione

A suspension of glycinamide, HCl (18.6 g, 168 mmol) in 500 ml of methanol was added to a solution of ninhydrin (30 g, 168 mmol) in 200 ml of methanol at −40° C. under stirring. After 20 min. a solution of sodium hydroxide (12 ml, 10N) was added dropwise at −40° C. to −30° C. over 25 min. and the temperature was slowly raised to −10° C. while stirring. After 2 hours a solution of sodium hydroxide (4 ml, 10N) was added dropwise and the mixture was stirred at −16° C. for 18 hours, then hydrochloric acid (360 ml, 1N) was added over 1.5 hours at −15° C. and the temperature was raised gradually to room temperature and stirred for 4 hours. The yellow precipitate was filtered off, washed with water and dried to give 24 g (72%) of the title compound. M.p.>300° C. $^1$H-NMR (DMSO-d$_6$, δ): 7.5–7.61 (m, 2H), 7.65 (t, 1H), 7.78 (d, 1H), 7.87 (s, 1H), 13.8 (s, 1H).

Analysis: Calculated for $C_{11}H_6N_2O_2$: C, 66.67; H, 3.05; N, 14.14%. Found: C, 66.88; H, 3.07; N, 14.51%.

EXAMPLE 2

9H-Indeno[1,2-b]pyrazine-2,3,9(1H,4H)-trione

9H-Indeno[1,2-b]pyrazine-3,9(4H)-dione (20 g, 100.9 mmol), recrystallized from acetic acid, was suspended in a mixture of 135 ml acetic acid and 135 ml acetic anhydride and hydrogen peroxide (9.8 ml, 35%) was added. After stirring overnight another portion (9.8 ml, 35%) of hydrogen peroxide was added. This was repeated five times over a week. The red precipitate was filtered off, washed with acetic acid and water and dried to give 18.5 g (79.6%) of the title compound, which could be further purified by dissolving in aqueous sodium hydroxide and precipitation by hydrochloric acid. M.p.>300° C. $^1$H-NMR (DMSO-d$_6$, δ): 7.15–7.45 (m, 4H), 12 (s, 1H), 12.8 (s, 1H).

Analysis: Calculated for $C_{11}H_6N_2O_3$. 0.9 $H_2O$: C, 57.35; H, 3.41; N, 12.16%. Found: C, 57.40; H, 3.44; N, 12.20%.

EXAMPLE 3

9-Hydroxyimino-9H-indeno[1,2-b]pyrazin-3(4H)-one

A mixture of 9H-indeno[1,2-b]pyrazine-3,9(4H)-dione (1.0 g, 5.0 mmol), pyridine (40 ml) and hydroxylamine hydrochloride (0.42 g, 6.0 mmol) was stirred at 80° C. for 18 hours. The reaction mixture was cooled to room temperature, and the precipitate was filtered off and washed with water, acetic acid and water and dried. The crude material (0.81 g) was recrystallized from DMF to afford 0.52 g (49%) of the title compound. M.p.>300° C. $^1$H-NMR (DMSO-d$_6$, δ): 7.49–7.62 (m, 2H), 7.88 (d, 1H), 7.95 (s, 1H), 8.36 (d, 1H), 12.5–13.2 (broad, 1H), 12.83 (s, 1H).

Analysis: Calculated for $C_{11}H_7N_3O_2$: C, 61.97; H, 3.31; N, 19.71%. Found: C, 62.29; H, 3.26; N, 19.44%.

EXAMPLE 4

(E)- and (Z)-9-Hydroxyimino-9H-indeno[1,2-b]pyrazine-2,3(1H,4H)-dione

A mixture of 9H-indeno[1,2-b]pyrazine-2,3,9(1H,4H)-trione,1H$_2$O (0.80 g, 3.46 mmol), pyridine (20 ml) and hydroxylamine hydrochloride (0.39 g, 5.6 mmol) was stirred at 70° C. for 3 hours. The reaction mixture was cooled to room temperature, and the precipitate was filtered off and washed with pyridine, 50% acetic acid and water and dried to give 0.41 g (51.7%) of the (E)-isomer of the title compound. M.p.>300° C. $^1$-NMR (DMSO-d$_6$, δ): 7.18 (t, 1H), 7.35 (t, 1H), 7.5 (d, 1H), 8.04 (d, 1H), 12.05 (s, 1H), 12.42 (s, 1H), 12.72 (s, 1H).

The mother liquor was evaporated in vacuo to dryness and 30 ml of 50% acetic acid was added to give 0.344 g of a mixture of (E)- and (Z)-isomers. From the filtrate it was possible by concentration to isolate 15 mg of the (Z)-isomer of the title compound. M.p.>300° C. $^1$-NMR (DMSO-d$_6$, δ): 7.2 (t, 1H), 7.33 (t, 1H), 7.54 (d, 1H), 7.57 (d, 1H, 10.92 (s, 1H), 12.63 (s, 2H).

EXAMPLE 5

(E)- and (Z)-9-Benzyloxyimino-9H-indeno[1,2-b]pyrazine-2,3(1H,4H)-dione

A mixture of 9H-indeno[1,2-b]pyrazine-2,3,9(1H,4H)-trione.1H$_2$O (1.0 g, 4.31 mmol), pyridine (30 ml) and O-benzylhydroxylamine hydrochloride (0.745 g, 4.67 mmol) was stirred at 80° C. for 18 hours. The reaction mixture was cooled to room temperature, and the precipitate was filtered off and washed with water, 50% acetic acid, water and dried to give 0.35 g (25.4%) as a mixture of (Z)- and (E)-isomers of the title compound containing (NMR) 67% of the (Z)-isomer and 33% of the (E)-isomer. M.p.>300° C. $^1$H-NMR, (Z)-isomer, (DMSO-d$_6$, δ): 5.33 (s, 2H), 7.2 (t, 1H), 7.29–7.58 (m, 8H), 11.32 (s, 1H), 12.69 (s, 1H).

Analysis: Calculated for C$_{18}$H$_{13}$N$_3$O$_3$: C, 67.71; H, 4.10; N, 13.16%. Found: C, 67.38; H, 4.04; N, 12.93%.

From the mother liquor another crop was filtered off. After suspension in 20 ml of 50% acetic acid the precipitate was filtered off, washed with water and dried to give 0.88 g (64%) of the title compound containing 7% of the (Z)-isomer and 93% of the (E)-isomer. M.p.>300° C. $^1$H-NMR, (E)-isomer, (DMSO-d$_6$, δ): 5.39 (S, 2H), 7.17 (t, 1H), 7.3–7.56 (m, 7H), 7.9 (d, 1H), 12.05 (s, 1H), 12.45 (s, 1H).

EXAMPLE 6

9H-Indeno[1,2-b]pyrazine-3,9(4H)-dione 9-ethylene acetal

A suspension of 9H-indeno[1,2-b]pyrazine-3,9(4H)-dione (1.0 g, 5.05 mmol) in ethylene glycol (10 ml), toluene (20 ml) and p-toluenesulfonic acid (20 mg) was refluxed with water separation for 18 hours. The reaction mixture was cooled to room temperature, ethanol (5 ml) was added and the precipitate was filtered off and washed with ethanol and dried to give 1.014 g (83%) of the title compound. M.p. 296°–298° C. $^1$H-NMR (DMSO-d$_6$, δ): 4.3–4.42 (m, 4H), 7.43–7.6 (m, 3H), 7.75 (d, 1H), 7.88 (s, 1H), 12.7 (s, 1H).

Analysis: Calculated for C$_{13}$H$_{10}$N$_2$O$_3$: C, 64.46; H, 4.16; N, 11.56%. Found: C, 64.62; H, 4.09; N, 11.35%.

EXAMPLE 7

9H-Indeno[1,2-b]pyrazine-2,3,9(1H,4H)-trione 9-ethylene acetal

A suspension of 9H-indeno[1,2-b]pyrazine-3,9(4H)-dione 9-ethylene acetal (4.0 g, 16.51 mmol) in a mixture of 30 ml of acetic acid and 30 ml of acetic anhydride and hydrogen peroxide (1.6 ml, 35%) was stirred overnight. Then another portion (1.6 ml, 35%) of hydrogen peroxide was added and stirring was continued overnight. That was repeated seven times over nine days.

After five days another portion (20 ml) of acetic anhydride was added. The precipitate was filtered off, washed with acetic acid and water and dried to give 1.57 g of the crude product, which was purified by suspension in a mixture of 1250 ml ethanol and 150 ml water, filtrated and dried to yield 0.728 g (17%) of the title compound. M.p. 296°–301° C. $^1$H-NMR (DMSO-d$_6$, δ): 4.25 (m, 2H), 4.32 (m, 2H), 7.12 (t, 1H), 7.28 (t, 1H), 7.33 (d, 1H), 7.41 (d, 1H), 12.0 (s, 1H), 12.3 (s, 1H).

Analysis: Calculated for: C$_{13}$H$_{10}$N$_2$O$_4$: C, 60.47; H, 3.90; N, 10.85%. Found: C, 60.31; H, 3.89; N, 10.43%.

EXAMPLE 8

9H-Indeno[1,2-b]pyrazine-3,9(4H)-dione 9-(2,2-dimethylpropylene) acetal

A suspension of 9H-indeno[1,2-b]pyrazine-3,9(4H)-dione (3.0 g, 15.14 mmol) in toluene (50 ml), 2,2-dimethyl-1,3-propanediol (10 g) and p-toluenesulfonic acid (30 mg) was refluxed with water separation for 140 hours. The reaction mixture was cooled to ambient temperature and ethanol (50 ml) was added. The precipitate was filtered off and washed with ethanol to give 3.68 g of the crude product, which was recrystallized from tetrahydrofuran to yield 2.34 g (54.4%) of the title compound. M.p. 281°–283° C. $^1$H-NMR (DMSO-d$_6$, δ): 0.9 (s, 3H), 1.39 (s, 3H), 3.58 (d, 2H), 4.57 (d, 2H), 7.5 (m, 2H), 7.63 (m, 1H), 7.73 (m, 1H), 7.89 (s, 1H), 12.4 (broad s, 1H).

Analysis: Calculated for C$_{16}$H$_{16}$N$_2$O$_3$: C, 67.59; H, 5.67; N, 9.85%. Found: C, 68.01; H, 5.74; N, 9.58%.

By concentration of the filtrate another crop 0.76 g (17.7%) of the title compound was isolated.

EXAMPLE 9

9H-Indeno[1,2-b]pyrazine-3,9(4H)-dione 9-(1,2-dimethylethylene) acetal

A suspension of 9H-indeno[1,2-b]pyrazine-3,9(4H)-dione (2.0 g, 10.09 mmol) in toluene (50 ml), 2,3-butanediol (20 ml) and p-toluenesulfonic acid (40 mg) was refluxed with water separation for 20 hours. The reaction mixture was evaporated in vacuo to dryness and another portion of toluene, 2,3-butanediol and p-toluenesulfonic acid was added and the mixture was refluxed again for 20 hours. After evaporation to dryness, the residue was suspended in ethanol (10 ml) and the precipitate was filtered off and washed with ethanol and dried to give 2.14 g (78.5%) of the title compound as a mixture of isomers. $^1$H-NMR (DMSO-d$_6$, δ): 1.24–1.4 (m, 6H), 4.03–4.87 (m, 2H), 7.42–7.91 (m, 5H), 12.6 (s, 1H).

EXAMPLE 10

9H-Indeno[1,2-b]pyrazine-2,3,9(1H,4H)-trione 9-(1,2-dimethylethylene) acetal

9H-Indeno[1,2-b]pyrazine-3,9(4H)-dione 9-(1,2-dimethylethylene) acetal (1.0 g, 3.7 mmol) was suspended in a mixture of 5 ml of acetic acid and 5 ml of acetic anhydride and hydrogen peroxide (0.50 ml, 30%) was added. After stirring overnight, another portion of hydrogen peroxide (0.20 ml, 30%) was added and the mixture was stirred for 20 hours. The precipitate was filtered off and washed with acetic acid and water to give 0.236 g of crude product, which was recrystallized from ethanol to yield 119 mg (11%) of the title compound, as a mixture of isomers. $^1$H-NMR (DMSO-d$_6$, δ): 1.2–1.4 (m, 6H), 4.3–4.8 (m, 2H), 7.12 (m, 1H), 7.27 (t, 1H), 7.34–7.48 (m, 2H), 11.83, 12.05 (2×s, 1H), 12.3 (s, 1H).

EXAMPLE 11

9-Hydroxy-9H-indeno[1,2-b]pyrazine-2,3(1H,4H)-dione

To a stirred suspension of 9H-indeno[1,2-b]pyrazine-2,3,9(1H,4H)-trione.-1H$_2$O (5.0 g, 21.5 mmol) in 200 ml of ethanol and 30 ml of water was added sodium borohydride (1.76 g, 46.5 mmol) in four portions over 2 hours, then 200 ml of water was added and the mixture was stirred for 18 hours at room temperature. The reaction mixture was acidified with hydrochloric acid (70 ml, 1N) to pH 1.5 and the precipitate was filtered off, washed with water and dried to give 4.59 g (91%) of the title compound. M.p.>300° C. $^1$H-NMR (DMSO-$d_6$, $\delta$): 5.1 (d, 1H), 5.72 (d, 1H), 7.15 (t, 1H), 7.28 (t, 1H), 7.41 (d, 1H), 7.48 (d, 1H), 12.0 (s, 1H), 12.25 (s, 1H).

Analysis: Calculated for $C_{11}H_8N_2O_3 \cdot 1 H_2O$: C, 56.41; H, 4.30; N, 11.96%. Found: C, 56.43; H, 4.35; N, 11.91%.

EXAMPLE 12

9-Hydroxy-9H-indeno[1,2-b]pyrazin-3(4H)-one

9H-Indeno[1,2-b]pyrazine-3,9(4H)-dione (5.0 g, 25.23 mmol) was reduced with sodium borohydride (1.72 g, 45.5 mmol) as described in example 11. Yield 5.29 g (96%) of the title compound. M.p. 251°–253° C. $^1$H-NMR (DMSO-$d_6$, $\delta$): 5.32 (d, 1H), 5.92 (d, 1H), 7.47 (m, 2H), 7.64 (m, 1H), 7.8 (m, 1H) 7.9 (s, 1H), 12.5 (s, 1H).

Analysis: Calculated for $C_{11}H_8N_2O_2 \cdot 1 H_2O$: C, 60.54; H, 4.62; N, 12.84%. Found: C, 60.69; H, 4.70; N, 12.73%.

EXAMPLE 13

9-Chloro-9H-indeno[1,2-b]pyrazin-3(4H)-one

9-Hydroxy-9H-indeno[1,2-b]pyrazin-3(4H)-one. $1H_2O$ (0.50 g, 2.29 mmol) was added to thionyl chloride (5 ml) under stirring. After 0.5 hours dichloromethane (10 ml) was added and the stirring was continued for 10 min. The precipitate was isolated by filtration and washed with dichloromethane, thereafter suspended in hydrochloric acid (10 ml, 0.5N), filtrated and dried to give 0.359 g (72%) of the title compound. M.p.>300° C. $^1$H-NMR (DMSO-$d_6$, $\delta$): 6.1 (s, 1H), 7.56 (m, 2H), 7.72 (m, 1H), 7.87 (m, 1H), 7.97 (s, 1H), 11.5–13.8 (broad s, 1H).

Analysis: Calculated for $C_{11}H_7N_2OCl$: C, 60.43; H, 3.23; N, 12.81; Cl, 16.21%. Found: C, 60.31; H, 3.26; N, 12.56; Cl, 16.07%.

EXAMPLE 14

9-Chloro-9H-indeno[1,2-b]pyrazine-2,3(1H,4H)-dione

9-Hydroxy-9H-indeno[1,2-b]pyrazine-2,3(1H,4H)-dione. $1H_2O$ (3.0 g, 12.8 mmol) was suspended in 30 ml of dichloromethane under stirring. Thionyl chloride (6 ml) was added and after cooling on an ice bath, pyridine (0.6 ml) was added over 5 min. After 15 min. at 0°–3° C. the temperature was elevated to room temperature and another 10 ml of dichloromethane was added. The mixture was stirred for 18 hours and the precipitate was filtered off and washed with dichloromethane to afford 2.91 g (97%) of the title Compound. M.p.>300° C. $^1$H-NMR (DMSO-$d_6$, $\delta$): 5.73 (s, 1H), 7.23 (t, 1H), 7.37 (t, 1H), 7.49 (d, 1H), 7.56 (d, 1H), 12.23 (s, 1H), 12.45 (s, 1H).

EXAMPLE 15

9-Acetoxy-9H-indeno[1,2-b]pyrazine-2,3(1H,4H)-dione

9-Chloro-9H-indeno[1,2-b]pyrazine-2,3(1H,4H)-dione (0.30 g, 1.28 mmol) was refluxed in 50 ml of acetic acid for 10 min. Activated carbon (100 mg) was added and the reaction mixture was filtered and evaporated in vacuo to about 3 ml, and 20 ml of water was added. The precipitate was filtered off and washed with water and dried to give 229 mg of the crude compound, which was recrystallized from acetic acid-water to yield 190 mg (57.5%) of the title compound. M.p.>300° C. $^1$H-NMR (DMSO-$d_6$, $\delta$): 2.13 (s, 3H), 6.36 (s, 1H), 7.15 (t, 1H), 7.29 (d, 1H) 7.35 (t, 1H), 7.5 (d, 1H), 12.0 (s, 1H), 12.4 (s, 1H).

EXAMPLE 16

9-Ethoxy-9H-indeno[1,2-b]pyrazine-2,3(1H,4H)-dione

9-Chloro-9H-indeno[1,2-b]pyrazine-2,3(1H,4H)-dione (0.50 g, 2.13 mmol) was refluxed in 25 ml dry ethanol for 7 hours. The mixture was evaporated to few ml and the precipitate was filtered off, washed with ethanol and dried to give 0.229 g of the crude compound, which was recrystallized from acetic acid-water to yield 0.131 g (25%) of the title compound. M.p.>300° C. $^1$H-NMR (DMSO-$d_6$, $\delta$): 1.1 (t, 3H), 3.25 (dq, 1H), 3.43 (dq, 1H), 5.22 (s, 1H), 7.17 (t, 1H), 7.33 (t, 1H), 7.42 (d, 1H), 7.51 (d, 1H), 12.1 (s, 1H), 12.31 (s, 1H).

EXAMPLE 17

9-Morpholino-9H-indeno[1,2-b]pyrazine-2,3(1H,4H)-dione

9-Chloro-9H-indeno[1,2-b]pyrazine-2,3(1H,4H)-dione (0.50 g, 2.13 mmol) was suspended in 5 ml of dry tetrahydrofuran, while cooling in an ice bath. Morpholine (0.37 ml, 4.27 mmol) dissolved in 2 ml of dry tetrahydrofuran was added over 2 min. After 1 hour the ice bath was removed and stirring was continued for 20 hours at room temperature. The precipitate was filtered off and washed with tetrahydrofuran, 10% acetic acid, water and dried to give 0.365 g of the crude product. Recrystallization from ethanol afforded 0.257 g (42%) of the title compound. M.p. 265°–267° C. $^1$H-NMR (DMSO-$d_6$, $\delta$): 2.47 (m, 2H), 2.61 (m, 2H), 3.56 (m, 4H), 4.54 (s, 1H), 7.13 (t, 1H), 7.3 (t, 1H), 7.47 (d, 1H), 7.53 (d, 1H), 11.8 (s, 1H), 12.25 (s, 1H).

EXAMPLE 18

9-(4-Methyl-1-piperazinyl)-9H-indeno[1,2-b]pyrazine-2,3(1H,4H)-dione

9-Chloro-9H-indeno[1,2-b]pyrazine-2,3(1H,4H)-dione (1.50 g, 6.39 mmol) was suspended in 15 ml of dry tetrahydrofuran, while cooling in an ice bath. N-Methylpiperazine (1.42 ml, 12.78 mmol) dissolved in 3 ml of dry tetrahydrofuran was added over 20 min, and the ice bath was removed and stirring was continued for 20 hours at room temperature. The precipitate was filtered off and washed with tetrahydrofuran and dried to give 2.42 g of a remanence, which was dissolved in 100 ml of boiling ethanol, and treated with 300 mg of activated carbon. The mixture was filtered and concentrated to 10 ml. The precipitate was filtered off, washed with ethanol and dried to give 0.65 g of the crude product. From the filtrate another crop of 0.57 g could be isolated. Recrystallization from 6M HCl afforded 0.73 g (30%) of the title compound as a dihydrochloride. M.p. 263°–265° C. $^1$H-NMR (DMSO-$d_{d6}$, $\delta$): 2.6 (m, 1H), 2.73 (s, 3H), 2.78–3.52 (m, 7H), 4.84 (s, 1H), 5.9–7.0 (broad, 2H), 7.2 (t, 1H), 7.35 (t, 1H), 7.48 (d, 1H), 7.58 (d, 1H), 10.92 (s, 1H), 11.76 (s, 1H), 12.34 (s, 1H).

Analysis: Calculated for: $C_{16}H_{20}N_4O_2Cl_2 \cdot \frac{1}{2}H_2O$: C, 50.53; H, 5.56; N, 14.73; Cl, 18.65%. Found: C, 50.53; H, 5.51; N, 14.53; Cl, 18.34%.

EXAMPLE 19

9-Dimethoxyphosphonyl-9H-indeno[1,2-b]pyrazine-2,3(1H,4H)-dione

9-Chloro9H-indeno[1,2-b]pyrazine-2,3(1H,4H)-dione (1.0 g, 4.26 mmol) and trimethyl phosphite (20 ml) were refluxed for 1 hour. The reaction mixture was evaporated in vacuo to dryness and triturated with 15 ml of methanol to give 0.355 g of the crude product. Recrystallization twice from methanol yield 0.25 g (19%) of the title compound. M.p. 252°–253° C. $^1$H-NMR (DMSO-$d_6$, $\delta$): 3.46 (d, 3H), 3.7 (d, 3H), 4.6 (d, 1H), 7.23 (t, 1H), 7.4 (t, 1H), 7.56 (d, 1H), 7.66 (d, 1H), 11.6 (s, 1H), 12.48 (s, 1H).

Analysis: Calculated for $C_{13}H_{13}N_2O_5P$: C, 50.66; H, 4.25; N, 9.09%. Found: C, 50.72; H, 4.41; N, 9.07%.

EXAMPLE 20

9-Diethoxyphosphonyl-9H-indeno[1,2-b]pyrazine-2,3(1H, 4H)-dione

9-Chloro-9H-indeno[1,2-b]pyrazine-2,3(1H,4H)-dione (1.0 g, 4.26 mmol) and triethyl phosphite (20 ml) was refluxed for 1 hour. The reaction mixture was evaporated in vacuo to dryness and triturated with 10 ml of ethanol to give 0.89 g of the crude product. Recrystallization from ethanol yield 0.62 g (43%) of the title compound. M.p. 248°–249° C. $^1$H-NMR (DMSO-$d_6$, $\delta$): 1.02 (t, 3H), 1.15 (t, 3H), 3.8 (m, 1H), 3.9 (m, 1H), 4.0 (m, 2H), 4.5 (d, 1H), 7.22 (t, 1H), 7.38 (t, 1H), 7.55 (d, 1H), 7.65 (d, 1H), 11.5 (s, 1H), 12.46 (s, 1H).

Analysis: Calculated for $C_{15}H_{17}N_2O_5P$: C, 53.57; H, 5.10; N, 8.33%. Found: C, 53.55; H, 5.29; N, 8.07%.

EXAMPLE 21

9-Phosphono-9H-indeno[1,2-b]pyrazine-2,3(1H, 4H)-dione

9-Diethoxyphosphonyl-9H-indeno[1,2-b]pyrazine-2,3 (1H, 4H)-dione (0.5 g, 1.49 mmol) was suspended in a mixture of acetonitril (30 ml) and bromotrimethylsilane (3 ml) and stirred overnight at 40° C. Then another portion of bromotrimethylsilane (3 ml) was added and stirring was continued at 50° C. for seven days. The reaction mixture was evaporated in vacuo to dryness and triturated with 10 ml of ethanol to give 0.39 g of the crude product. Purification was performed by dissolving in a mixture of 15 ml of water and 20 ml of saturated sodium hydrogen carbonate solution and precipitation with about 6 ml 6M hydrochloric acid to pH 1.0. The yield was 0.28 g (60%) of the title compound as mono sodium salt. M.p.>300° C. $^1$H-NMR ($D_2O$, $\delta$): 4.2 (d, 1H), 7.35 (t, 1H), 7.45 (t, 1H), 7.5 (d, 1H), 7.72 (d, 1H).

Analysis: Calculated for $C_{11}H_8N_2O_5PNa \cdot \frac{1}{2}H_2O$: C, 42.46; H, 2.92; N, 9.00%. Found: C, 42.18; H, 3.16; N, 8.72%.

EXAMPLE 22

2-Phenyl-9H-indeno[1,2-b]pyrazine-3,9(4H)-dione

2-Phenylglycinamide, HCl (5.22 g, 28 mmol) was reacted with ninhydrin (5.0 g, 28 mmol) following the procedure outlined in example 1. The crude product (4.73 g) was recrystallized from acetic acid to give 3.7 g (48%) of the title compound. M.p.>300° C. $^1$H-NMR (DMSO-$d_6$, $\delta$): 7.45–7.68 (m, 6H), 7.81 (d, 1H), 8.25 (m, 2H), 14.0 (s, 1H).

Analysis: Calculated for $C_{17}H_{10}N_2O_2$: C, 74.45; H, 3.67; N, 10.27%. Found: C, 74.37; H, 3.73; N, 9.91%.

EXAMPLE 23

2-Phenyl-9H-indeno[1,2-b]pyrazine-3,9(4H)-dione 9-ethylene acetal

2-Phenyl-9H-indeno[1,2b]pyrazine-3,9(4H)-dione (0.90 g, 3.28 mmol) was reacted with ethylene glycol (9 ml) following the procedure outlined in example 6. The crude product (0.93 g) was recrystallized from tetrahydrofuran/heptane to give 0.53 g (51%) of the title compound. M.p. 296°–296.5° C. $^1$H-NMR (DMSO-$d_6$, $\delta$): 4.32–4.5 (m, 4H), 7.4–7.6 (m, 6H), 7.8 (d, 1H), 8.3 (m, 2H), 13.48 (s, 1H).

Analysis: Calculated for $C_{19}H_{14}N_2O_3$: C, 71.69; H, 4.43; N, 8.80%. Found: C, 71.95; H, 4.41; N, 8.77%.

EXAMPLE 24

9-Hydroxy-9-phenyl-9H-indeno[1,2-b]pyrazin-3(4H)-one

9H-Indeno[1,2-b]pyrazine-3,9(4H)-dione (2 g) was dissolved in dry THF (50 ml). Triethylamine (1.6 ml) was added and trimethylsilyl chloride (1.4 ml) dissolved in THF (10 ml) was added dropwise at room temperature. The mixture was stirred overnight and the precipitate filtered off. Phenylmagnesium bromide (20 mmol) in THF (10 ml) was subsequently added dropwise under nitrogen, and the resulting mixture stirred at room temperature for 3 days. Subsequent evaporation followed by addition of water and addition of HCl (1N) to slightly acidic solution resulted in precipitation of yellow crystals (2.7 g). The precipitate was purified on silica gel column using methylene chloride/methanol (9/1) as eluent resulting in 1.2 g pure title compound. M.p.>270° C. The MS showed the molecular ion 276. $^1$H-NMR (DMSO-$d_6$, $\delta$): 6.39 (s, 1H), 7.15–7.5 (m, 8H), 7.82 (s+m, 2H), 12.6 (s, 1H).

EXAMPLE 25

9-Acetoxy-9-phenyl-9 H-indeno[1,2-b]pyrazin-3 (4H)-one

9-Hydroxy-9-phenyl-9H-indeno[1,2-b]pyrazin-3(4H)-one (0.24 g) was stirred with a mixture of acetic acid (3 ml), acetic anhydride (3 ml) and hydrogen peroxide (0.42 ml) at room temperature for 3 weeks. The resulting very complex mixture was evaporated and treated with water resulting in precipitation of 200 mg of a crystalline mixture. Purification on silica gel column using methylene chloride/methanol: (9/1) as eluent resulted in 70 mg of a compound which was recrystallized from ethanol. Yield 40 mg of the title compound. M.p. 220°–223° C. MS showed the molecular ion 318 and a degradation pattern in accordance with the title compound. $^1$H-NMR ($CDCl_3$/$CD_3OD$: 9/1, $\delta$): 2.4–2.5 (3H, s), 7.3–7.6 (9H, m), 7.9–8.0 (1H, m), 8.2 (1H, s).

EXAMPLE 26

9-(2-Methoxyethoxy)-9H-indeno[1,2-b]pyrazine-2,3 (1H, 4H)-dione

A suspension of 9-hydroxy-9H-indeno[1,2-b]pyrazine-2,3(1H, 4H)-dione. $1H_2O$ (0.50 g, 2.13 mmol) in benzene (20 ml), 2-methoxyethanol (10 ml) and p-toluensulfonic acid (20 mg) was refluxed with water separation for 20 hours. The reaction mixture was evaporated in vacuo to dryness, the residue was suspended in ethanol (10 ml) and the precipitate was filtered off and washed with ethanol and dried to give 0.48 g of the crude product, which was recrystallized from ethanol to yield 0.35 g (60%) of the title compound. M.p.>300° C. $^1$-NMR (DMSO-d$_6$, δ): 3.22 (s, 3H), 3.27–3.51 (m, 4H), 5.24 (s, 1H), 7.18 (t, 1H), 7.33 (t, 1H), 7.42 (d, 1H), 7.5 (d, 1H), 12.06 (s, 1H), 12.29 (s, 1H).

EXAMPLE 27

9H-Indeno[1,2-b]pyrazine-3,9(4H)-dione 9-ethylene dithioacetal

A suspension of 9H-indeno[1,2-b]pyrazine-3,9(4H)-dione (0.50 g, 2.52 mmol) in benzene (10 ml), 1,2-ethanedithiol (0.63 ml, 7.56 mmol) and boron trifluoride etherate (0.31 ml, 2.52 mmol) was refluxed for 23 hours. The reaction mixture was cooled to room temperature, and the precipitate was filtered off and washed with benzene and water and dried. The crude material (0.64 g) was recrystallized twice from ethanol to give 0.44 g (64%) of the title compound. M.p. 284°–290° C. $^1$-NMR (DMSO-d$_6$, δ): 3.75–3.94 (m, 4H), 7.46–7.57 (m, 2H), 7.8 (m, 2H), 7.95 (s, 1H), 12.6 (s, 1H).

EXAMPLE 28

9H-Indeno[1,2-b]pyrazine-2,3,9(1H, 4H)-trione 9-ethylene dithioacetal

A suspension of 9H-indeno[1,2-b]pyrazine-2,3,9(1H, 4H)-trione. 0.9 H$_2$O (2.0 g, 8.68 mmol) in toluene (50 ml), 1,2-ethanedithiol (2.19 ml, 26.04 mmol) and boron trifluoride etherate (1.07 ml, 8.68 mmol) was refluxed for 20 hours. The reaction mixture was cooled to room temperature, and the precipitate was filtered off and washed with toluene, ethanol-water (2:1) and ethanol. The crude material (2.40 g) was recrystallized from DMF-water to give 2.09 g (83%) of the title, compound. M.p.>300° C. $^1$H-NMR (DMSO-d$_6$, δ): 3.68 (m, 2H), 3.91 (m, 2H), 7.2 (t, 1H), 7.3 (t, 1H), 7.51 (d, 1H), 7.59 (d, 1H), 12.05 (s, 1H), 12.38 (s, 1H).

Analysis: Calculated for C$_{13}$H$_{10}$N$_2$O$_2$S$_2$: C, 53.78; H, 3.47; N, 9.65; S, 22.08%. Found: C, 53.43; H, 3.58; N, 9.55; S, 21.84%.

EXAMPLE 29

9-(3,3-Diphenylpropoxy)-9H-indeno[1,2-b]pyrazine-2,3(1H, 4H)-dione

A suspension of 9-hydroxy-9H-indeno[1,2-b]pyrazine-2,3(1H, 4H)-dione. 1H$_2$O (1.0 g, 4.26 mmol) in benzene (40 ml), 3,3-diphenyl-1-propanol (10 ml) and p-toluensulfonic acid (40 mg) was refluxed with water separation for 48 hours. The reaction mixture was evaporated in vacuo to dryness, the residue was suspended in ethanol (10 ml) and the precipitate was filtered off and washed with ethanol and dried to give 0.224 g (12.5%) of the title compound. M.p. 224°–228° C. $^1$H-NMR(DMSO-d$_6$, δ): 2.14–2.32 (m, 2H), 3.0–3.22 (m, 2H), 4.13 (t, 1H), 5.22 (s, 1H), 7.0–7.5 (m, 14H), 12.12 (s, 1H), 12.26 (s, 1H).

Analysis: Calculated for C$_{26}$H$_{22}$N$_2$O$_3$.½H$_2$O: C, 74.45; H, 5.53; N, 6.68%. Found: C, 74.37; H, 5.58; N, 6.28%.

EXAMPLE 30

9-(2,2-Bis(4-chlorophenyl))ethoxy-9H-indeno[1,2-b]pyrazine-2,3(1H, 4H)-dione A suspension of 9-hydroxy-9H-indeno[1,2-b]pyrazine-2,3(1H, 4H)-dione. 1H$_2$O (0.50 g, 2.13 mmol) in acetic acid (30 ml), 2,2-bis(4-chlorophenyl)ethanol (2.84 g, 10.65 mmol) and p-toluensulfonic acid (20 mg) was refluxed for 21 hours. The reaction mixture was evaporated in vacuo to dryness, the residue was suspended in ethanol (40 ml) and the precipitate was filtered off and washed with ethanol and dried to give 0.39 g of the crude product, which was recrystallized from ethanol to yield 0.174 g (17.5%) of the title compound. M.p. 234°–237° C. $^1$-NMR (DMSO-d$_6$, δ): 3.68 (t, 1H), 4.0 (t, 1H), 4.27 (t, 1H), 5.23 (s, 1H), 7.1–7.5 (m, 12H), 11.98 (s, 1H), 12.25 (s, 1H).

Analysis: Calculated for C$_{25}$H$_{18}$N$_2$O$_3$Cl$_2$: C, 64.53; H, 3.90; N, 6.02%. Found: C, 64.30; H, 3.98; N, 5.95%.

EXAMPLE 31

9-(4-(2-Hydroxyethyl)-1-piperazinyl)-9H-indeno[1,2-b]pyrazine-2,3(1H, 4H)-dione 9-Chloro-9H-indeno[1,2-b]pyrazine-2,3(1H, 4H)-dione (3.0 g, 12.8 mmol) was reacted with N-(2-hydroxyethyl) piperazine (3 66 g, 28.2 mmol) as described in example 18. The crude product was purified by dissolving in aqueous NaHCO$_3$/NaOH and precipitated by adding to hydrochloric acid. The procedure was repeated and the product was finally washed with ethanol and dried to give 1.53 g (28%) of the title compound as a dihydrochloride M.p. 210° C. (destruction). $^1$-NMR (DMSO-d$_6$+D$_2$O, δ): 2.35–3.6 (m, 10H), 3.75 (m, 2H), 4.73 (s, 1H), 7.22 (t, 1H), 7.35 (t, 1H), 7.51 (d,1H), 7.57 (d, 1H).

Analysis: Calculated for C$_{17}$H$_{22}$N$_4$O$_3$Cl$_2$-1¼H$_2$O: C, 48.18; H, 5.83; N, 13.22; Cl, 16.73%. Found: C, 48.18; H, 6.04; N, 12.98; Cl, 16.45%.

EXAMPLE 32

9-(4-(2-Methoxyphenyl)-1-piperazinyl)-9H-indeno[1,2-b]pyrazine-2,3(1H, 4H)-dione 9-Chloro-9H-indeno[1,2-b]pyrazine-2,3(1H, 4H)-dione (3.0 g, 12.8 mmol) was suspended in 50 ml of dry tetrahydrofuran, while cooling in an ice bath. 1-(2-Methoxyphenyl)piperazine. HCl (6.5 g, 28.2 mmol) was added and triethylamine (3.9 ml, 28.2 mmol) was added over 15 min., and the ice bath was removed and stirring was continued for 20 hours at room temperature. The precipitate was filtered off, washed with tetrahydrofuran and dissolved in a mixture of 500 ml ethanol and 300 ml tetrahydrofuran by boiling and treated with 500 mg of activated carbon. The mixture was filtered, 10 ml of 6M HCl was added and the mixture was concentrated to about 100 ml. The precipitate was filtered off, washed with ethanol and dried to give 3.79 g of the crude product, which was purified by dissolving in 50 ml 1M NaOH and precipitated by adding to 100 ml 1M HCl. The product was filtered off and washed with 1M HCl and dried to yield 1.86 g (31.7%) of the title compound as a hydrochloride. M.p. 235°–238° C. $^1$-NMR (DMSO-d$_6$+D$_2$O, δ): 3.0–3.5 (m, 8H), 3.8 (s, 3H), 5.23 (s, 1H), 7.0 (t, 1H), 7.08 (d, 1H), 7.2 (m, 2H), 7.34 (t, 1H), 7.48 (t, 1H), 7.63 (d, 1H), 7.75 (d, 1H).

Analysis: Calculated for C$_{22}$H$_{23}$N$_4$O$_3$Cl.1¾H$_2$O: C, 57.64; H, 5.83; N; 12.22; Cl, 7.73%. Found: C, 57.79; H, 5.56; N, 12.13; Cl, 8.05%.

EXAMPLE 33

9-(4-Diphenylmethyl-1-piperazinyl)-9H-indeno[1,2-b]pyrazine-2,3(1H, 4H)-dione 9-Chloro-9H-indeno[1,2-b]pyrazine-2,3(1H, 4H)-dione (1.0 g, 4.26 mmol) was suspended in 10 ml of dry tetrahydrofuran, while cooling in an ice bath. 1-(Diphenylmethyl)piperazine (1.1 g, 4.26 mmol) dissolved in 10 ml of dry tetrahydrofuran was added over 10 min., thereafter triethylamine (0.59 ml, 4.26 mmol) in 3 ml tetrahydrofuran was added. The ice bath was removed and stirring was continued for 20 hours at room temperature. The precipitate was filtered off and washed with tetrahydrofuran to give 1.36 g of the crude product which was recrystallized two times from acetic acid to yield 0.45 g (20%) of the title compound as a hydrochloride. M.p. 212°14 216° C. $^1$H-NMR (DMSO-d$_6$, δ): 2.5–3.3 (m, 8H), 4.64 (s, 1H), 5.62 (d, 1H), 7.1–7.9 (m, 14H), 11.25 (s, 1H), 11.74 (s, 1H), 12.25 (s, 1H).

Analysis: Calculated for $C_{28}H_{27}N_4O_2Cl.2H_2O$: C, 64.30; H, 5.97; N, 10.71; Cl, 6.78%. Found: C, 64.36; H, 5.78; N, 10.24; Cl, 6.73%.

EXAMPLE 34

9-(1-Piperazinyl)-9H-indeno[1,2-b]pyrazine-2,3(1H, 4H)-dione

Piperazine (1.1 g, 12.8 mmol) was suspended in 15 ml of dry tetrahydrofuran at −20° C. 9-Chloro-9H-indeno[1,2-b]pyrazine-2,3(1H, 4H)-dione (1.5 g, 6.4 mmol) was added over 25 min. and the temperature was slowly rised to room temperature while stirring. After 20 hours another portion of piperazine (0.55 g, 6.4 mmol) was added and stirring was continued for 72 hours. The reaction mixture was evaporated in vacuo to dryness and the remanence was suspended in 10 ml 6M HCl. The product was filtered off and washed with 1M HCl and dried to give 1.7 g of the crude product, which was purified by dissolving in aqueous sodium hydroxide and precipitated by adding to hydrochloric acid. The procedure was repeated and the product was finally washed with ethanol and dried to give 0.64 g (27%) of the title compound as a hydrochloride. M.p. 259°–263° C. $^1$H-NMR (DMSO-d$_6$, δ): 2.65–3.15 (m, 8H), 4.7 (s, 1H), 7.17 (t, 1H), 7.34 (t, 1H), 7.45 (d, 1H), 7.57 (d, 1H), 8.93 (s, 2H), 11.8 (s, 1H), 12.3 (s, 1H).

EXAMPLE 35

9-(2-Aminoethylthio)-9H-indeno[1,2-b]pyrazine-2,3(1H, 4H)-dione

9-Hydroxy-9H-indeno[1,2-b]pyrazine-2,3(1H, 4H)-dione. 1H$_2$O (0.5 g, 2.13 mmol), aminoethanethiol hydrochloride (0.48 g, 4.26 mmol) and boron trifluoride etherate (0.29 ml, 2.34 mmol) was refluxed in 10 ml of acetic acid for 24 hours. Another portion of aminoethanethiol hydrochloride (0.48 g, 4.26 mmol) was added and the reaction mixture was refluxed for 24 hours. The reaction mixture was cooled to room temperature, and the precipitate was filtered off and washed with acetic acid and water and dried. The crude material (0.59 g) was purified by dissolving in aqueous sodium hydroxide and precipitated by adding to hydrochloric acid. The product was finally washed with ethanol containing a small amount of aqueous hydrochloric acid and dried to give 0.377 g (55%) of the title compound as a hydrochloride. M.p. 297°–298° C. $^1$H-NMR (DMSO-d$_6$, δ): 2.2–2.5 (m, 2H), 2.55–2.8 (m, 2H), 4.85 (s, 1H), 7.22 (t, 1H), 7.34 (t, 1H), 7.52 (d, 1H), 7.61 (d, 1H), 7.92 (s, 3H), 12.03 (s, 1H), 12.4 (s, 1H).

EXAMPLE 36

9-(2-Diethylaminoethylthio)-9H-indeno[1,2-b]pyrazine-2,3(1H, 4H)-dione

9-Hydroxy-9H-indeno[1,2-b]pyrazine-2,3(1H, 4H)-dione. 1H$_2$O (1.0 g, 4.26 mmol), 2-diethylaminoethanethiol hydrochloride (1.44 g, 8.52 mmol) and boron trifluoride etherate (0.53 ml, 4.26 mmol) were refluxed in 20 ml of acetic acid for 3 hours. After stirring overnight at room temperature the reaction mixture was evaporated in vacuo to dryness, the remanence was suspended in ethyl acetate, filtrated and washed with ethyl acetate and ethanol to give 0.96 g of crude product, which was recrystallized from acetic acid to yield 0.59 g (37%) of the title compound as a hydrochloride. M.p. 221°–225° C. $^1$H-NMR (DMSO-d$_6$, δ): 0.98 (m, 6H), 2.4–2.68 (m, 2H), 2.82–2.95 (m, 4H), 3.35 (s, 2H), 4.87 (s, 1H), 7.22 (t, 1H), 7.34 (t, 1H), 7.53 (d, 1H), 7.59 (d, 1H), 10.18 (s, 1H), 12.06 (s, 1H), 12.36 (s, 1H).

Analysis: Calculated for $C_{17}H_{22}N_3O_2SCl.\frac{1}{4}H_2O$: C, 54.83; H, 6.09; N, 11.28%. Found: C, 54.83; H, 6.10; N, 11.20%.

EXAMPLE 37

9H-Indeno[1,2-b]pyrazine-2,3,9(1H, 4H)-trione 9-ethylene dithioacetal monosulfoxide 9H-Indeno[1,2-b]pyrazine-2,3,9(1H, 4H)-trione 9-ethylene dithioacetal (0.5 g, 1.72 mmol) was suspended in a mixture of 10 ml of acetic acid and 10 ml of acetic anhydride. Hydrogen peroxide 35% (0.18 ml, 1.89 mmol) was added and the mixture was stirred overnight at room temperature. The precipitate was filtered off and washed with acetic acid and dried to give 0.38 g of crude product, which was recrystallized from acetic acid to yield 0.16 g (29%) of the title compound. $^1$H-NMR (DMSO-d$_6$, δ): 3.58–3.72 (m, 1H), 3.8–3.96 (m, 2H), 4.32–4.48 (m, 1H), 7.25 (t, 1H), 7.41 (t, 1H), 7.5 1H), 7.64 (d, 1H), 11.86 (s, 1H), 12.55 (s, 1H).

EXAMPLE 38

9-Hydroxy-9-phenyl-9H-indeno[1,2-b]pyrazine-2,3 (1H, 4H)-dione

9H-Indeno[1,2-b]pyrazine-2,3,9(1H, 4H)-trione. 1H$_2$O (2.31 g, 10.0 mmol) was suspended in a mixture of 100 ml of tetrahydrofuran and 100 ml of toluene and evaporated to dryness. Dry tetrahydrofuran (100 ml), trimethylsilyl chloride (2.8 ml, 21 mmol) and triethylamine (3.1 ml, 21 mmol) were added and the mixture was refluxed overnight. After cooling to room temperature, the precipitate was filtered off and phenylmagnesium bromide (21.0 mmol) in ether (7 ml) was subsequently added dropwise, and the resulting mixture stirred at room temperature for 3 days. Subsequent evaporation to 50 ml followed by addition to 350 ml ice-cold 1M HCl resulted in precipitation of crystals (2.93 g). The precipitate was recrystallized from methanol/water to give 1.47 g (50%) of the title compound. M.p. 243°–253° C. $^1$H-NMR (DMSO-d$_6$, δ): 6.26 (s, 1H), 7.0–7.45 (m, 8H), 7.51 (d, 1H), 11.8 (s, 1H), 12.34 (s, 1H).

Analysis: Calculated for $C_{17}H_{12}N_2O_3.\frac{1}{2}H_2O$: C, 67.77; H, 4.35; N, 9.30%. Found: C, 67.84; H, 4.36; N, 8.98%.

EXAMPLE 39

9-Ethoxy-9-phenyl-9H-indeno[1,2-b]pyrazine-2,3 (1H, 4H)-dione

9-Hydroxy-9-phenyl-9H-indeno[1,2-b]pyrazine-2,3(1H, 4H)-dione. ½ H$_2$O (0.20 g, 0.66 mmol), benzene (10 ml), ethanol (10 ml) and p-toluensulfonic acid (20 mg) were refluxed with water separation overnight. The reaction mixture was evaporated in vacuo to dryness, the remanence was suspended in water (20 ml) and the precipitate was filtered off and dried to give 0.20 g of the crude product, which was purified by fractionated crystallization from acetic acid/water to yield 0.127 g (60%) of the title compound. M.p. 230° C. (destruction). ¹H-NMR (DMSO-d₆, δ): 1.12 (m, 3H), 2.98–3.35 (m, 2H), 7.0–7.6 (m, 9H), 11.9 (s, 1H), 12.4 (s, 1H).

EXAMPLE 40

2-Hydroxymethyl-9H-indeno[1,2-b]pyrazine-3,9 (4H)-dione

Serinamide.HCl (3.0 g, 21.34 mmol) was reacted with ninhydrin (3.8 g, 21.34 mmol) following the procedure outlined in example 1. The crude product (1.86 g) was dissolved in aqueous NaHCO₃ and added to hydrogen chloride in 90% ethanol. The precipitate was filtered off and washed with ethanol and water and dried to yield 1.65 g (34%) of the title compound. M.p.>300° C. ¹H-NMR (DMSO-d₆, δ): 4.5 (s, 2H), 5.08 (broad, 1H), 7.45–7.8 (m, 4H), 13.8 (s, 1H).

Analysis: Calculated for C₁₂H₈N₂O₃.0.1 H₂O: C, 62.66; H, 3.59; N, 12.18%. Found: C, 62.52; H, 3.43; N, 12.24%.

We claim:

1. A compound of formula (I) or a tautomeric form thereof

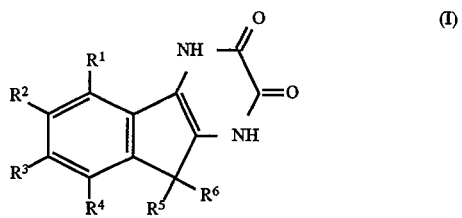

wherein
R¹, R², R³ and R⁴ independently are hydrogen, halogen, C₁₋₆-alkyl or C₁₋₆-alkoxy; and
R⁵ is hydrogen; hydroxy; halogen; cyano; C₁₋₆-alkyl optionally substituted with hydroxy; C₁₋₆-alkoxy optionally substituted with one or two phenyl group(s) wherein the phenyl group(s) is/are optionally substituted with halogen; C₁₋₆-(alkoxyalkoxy); C₁₋₆-thioalkyl optionally substituted with an amino group wherein the amino group is optionally mono or disubstituted with C₁₋₆-alkyl; C₁₋₆-acyloxy; phosphono; C₁₋₆-alkoxy disubstituted phosphonyl; or a morpholino or piperazinyl group which is optionally substituted with a C₁₋₆-alkyl group wherein the alkyl group is optionally substituted by hydroxy or wherein the morpholino or piperazinyl group is optionally substituted with one or two phenyl group(s) wherein the phenyl group(s) is/are optionally substituted with methoxy; and R⁶ is hydrogen, C₆-alkyl or phenyl; or R⁵ and R⁶ together represent a carbonyl group, a hydroxyimino group or a benzyloxyimino group; or
a pharmaceutically acceptable salt thereof.

2. A compound according to claim 1, wherein R¹, R², R³ and R⁴ independently are H.

3. A compound according to claim 1, wherein R⁵ and R⁶ together represent a carbonyl group, a hydroxyimino group or a benzyloxyimino group.

4. A compound according to claim 1, wherein R⁵ is hydrogen; hydroxy; halogen; cyano; C₁₋₆-alkyl optionally substituted with hydroxy; C₁₋₆-alkoxy optionally substituted with one or two phenyl group(s) wherein the phenyl group (s) is/are optionally substituted with halogen; C₁₋₆- (alkoxyalkoxy); C₁₋₆-thioalkyl optionally substituted with an amino group wherein the amino group is optionally mono or disubstituted with C₁₋₆-alkyl; C₁₋₆-acyloxy; phosphono; C₁₋₆-alkoxy disubstituted phosphonyl; or a morpholino or piperazinyl group which is optionally substituted with a C₁₋₆-alkyl group wherein the alkyl group is optionally substituted by hydroxy or wherein the morpholino or piperidinyl group is optionally substituted with one or two phenyl group(s) wherein the phenyl group(s) is/are optionally substituted with methhoxy; and R⁶ is hydrogen, C₁₋₆-alkyl or phenyl.

5. A compound according to claim 1 which is:
9H-Indeno[1,2-b]pyrazine-2,3,9(1H,4H)-trione; or
a pharmaceutically acceptable salt thereof.

6. A compound according to claim 1 which is:
(E)-9-Hydroxyimino-9H-indeno[1,2-b]pyrazine-2,3(1H, 4H)-dione;
(Z)-9-Hydroxyimino-9H-indeno[1,2-b]pyrazine-2,3(1H, 4H)-dione;
(E)-9-Benzyloxyimino-9H-indeno[1,2-b]pyrazine-2,3 (1H,4H)-dione;
(Z)-9-Benzyloxyimino-9H-indeno[1,2-b]pyrazine-2,3 (1H,4H)-dione; or
a pharmaceutically acceptable salt thereof.

7. A compound according to claim 1 which is:
9-Chloro-9H-indeno[1,2-b]pyrazine-2,3(1H,4H)-dione; or
a pharmaceutically acceptable salt thereof.

8. A compound according to claim 1 which is:
9-Hydroxy-9H-indeno[1,2-b]pyrazine-2,3(1H,4H)-dione;
9-Acetoxy-9H-indeno[1,2-b]pyrazine-2,3(1H,4H)-dione;
9-Ethoxy-9H-indeno[1,2-b]pyrazine-2,3(1H,4H)-dione;
9-(2-Methoxyethoxy)-9H-indeno[1,2-b]pyrazine-2,3(1H, 4H)-dione;
9-(3,3-Diphenylpropoxy)-9H-indeno[1,2-b]pyrazine-2,3 (1H, 4H)-dione;
9-(2,2-Bis(4-chlorophenyl))ethoxy-9H-indeno[1,2-b] pyrazine-2,3(1H, 4H)-dione; or
a pharmaceutically acceptable salt thereof.

9. A compound according to claim 1 which is:
9-(2-Aminoethylthio)-9H-indeno[1,2-b]pyrazine-2,3(1H, 4H)-dione;
9-(2-Diethylaminoethylthio)-9H-indeno[1,2-b]pyrazine-2,3(1H,4H)-dione; or
a pharmaceutically acceptable salt thereof.

10. A compound according to claim 1 which is:
9-Dimethoxyphosphonyl-9H-indeno[1,2-b]pyrazine-2,3 (1H,4H)-dione;
9-Diethoxyphosphonyl-9H-indeno[1,2-b]pyrazine-2,3 (1H, 4H)-dione;
9-Phosphono-9H-indeno[1,2-b]pyrazine-2,3(1H, 4H)-dione; or
a pharmaceutically acceptable salt thereof.

11. A compound according to claim 1 which is:
9-Morpholino-9H-indeno[1,2-b]pyrazine-2,3(1H,4H)-dione; or
a pharmaceutically acceptable salt thereof.

12. A compound according to claim 1 which is:
9-(4-Methyl-1-piperazinyl)-9H-indeno[1,2-b]pyrazine-2,3(1H,4H)-dione;
9-(4-(2-Hydroxyethyl)-1-piperazinyl)-9H-indeno[1,2-b] pyrazine-2,3(1H,4H)-dione;
9-(4-(2-Methoxyphenyl)-1-piperazinyl)-9H-indeno[1,2-b]pyrazine-2,3(1H, 4H)-dione;

9-(1-Piperazinyl)-9H-indeno[1,2-b]pyrazine-2,3(1H,4H)-dione; or a pharmaceutically acceptable salt thereof.

13. A compound according to claim 1 which is:

9-Hydroxy-9-phenyl-9H-indeno[1,2-b]pyrazine-2,3(1H,4H)-dione;

9-Ethoxy-9-phenyl-9H-indeno[1,2-b]pyrazine-2,3(1H,4H)-dione; or a pharmaceutically acceptable salt thereof.

14. A pharmaceutical composition comprising a compound according to claim 1 together with a pharmaceutically acceptable carrier or diluent.

15. The pharmaceutical composition according to claim 14 in the form of an oral dosage unit or parenteral dosage unit.

16. The pharmaceutical composition according to claim 15 in the form of an oral dosage unit containing about 1–200 mg of the compound.

17. A compound of formula (I) or a tautomeric form thereof

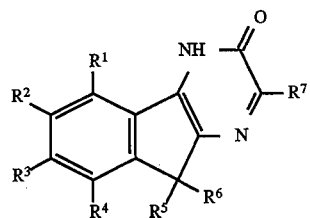

wherein $R^1$, $R^2$, $R^3$ and $R^4$ independently are hydrogen, halogen, $C_{1-6}$-alkyl or $C_{1-6}$-alkoxy;

$R^5$ is hydrogen; hydroxy; halogen; cyano; $C_{1-6}$-alkyl optionally substituted with hydroxy; $C_{1-6}$-alkoxy optionally substituted with one or two phenyl group(s) wherein the phenyl group(s) is/are optionally substituted with halogen; $C_{1-6}$-(alkoxyalkoxy); $C_{1-6}$-thioalkyl optionally substituted with an amino group wherein the amino group is optionally mono or disubstituted with $C_{1-6}$-alkyl; $C_{1-6}$-acyloxy; phosphono; $C_{1-6}$-alkoxy disubstituted phosphonyl; or a morpholino or piperazinyl group which is optionally substituted with a $C_{1-6}$-alkyl group wherein the alkyl group is optionally substituted by hydroxy or wherein the morpholino or piperazinyl group is optionally substituted with one or two phenyl group(s) wherein the phenyl group(s) is/are optionally substituted with methoxy; and $R^6$ is hydrogen, $C_{1-6}$-alkyl or phenyl; or $R^5$ and $R^6$ together represent a carbonyl group, a hydroxyimino group or a benzyloxyimino group; and $R^7$ is phenyl or —$CH_2OR^8$ wherein $R^8$ is hydrogen or benzyl; or a pharmaceutically acceptable salt thereof.

18. A compound according to claim 17, wherein $R^1$, $R^2$, $R^3$ and $R^4$ independently are H.

19. A compound according to claim 17, wherein $R^5$ and $R^6$ together represent a carbonyl group, a hydroxyimino group or a benzyloxyimino group.

20. A compound according to claim 17, wherein $R^5$ is hydrogen; hydroxy; halogen; cyano; $C_{1-6}$-alkyl optionally substituted with hydroxy; $C_{1-6}$-alkoxy optionally substituted with one or two phenyl group(s) wherein the phenyl group (s) is/are optionally substituted with halogen; $C_{1-6}$-(alkoxyalkoxy); $C_{1-6}$-thioalkyl optionally substituted with an amino group wherein the amino group is optionally mono or disubstituted with $C_{1-6}$-alkyl; $C_{1-6}$-acyloxy; phosphono; $C_{1-6}$-alkoxy disubstituted phosphonyl; or a morpholino or piperazinyl group which is optionally substituted with a $C_{1-6}$-alkyl group wherein the alkyl group is optionally substituted by hydroxy or wherein the morpholino or piperidinyl group is optionally substituted with one or two phenyl group(s) wherein the phenyl group(s) is/are optionally substituted with methoxy; and $R^6$ is hydrogen, $C_{1-6}$-alkyl or phenyl.

21. A compound according to claim 17 which is:

2-Phenyl-9H-indeno[1,2-b]pyrazine-3,9(4H)-dione;
2-Hydroxymethyl-9H-indeno[1,2-b]pyrazine-3,9(4H)-dione; or a pharmaceutically acceptable salt thereof.

22. A pharmaceutical composition comprising a compound according to claim 17 together with a pharmaceutically acceptable carrier or diluent.

23. The pharmaceutical composition according to claim 22 in the form of an oral dosage unit or parenteral dosage unit.

24. The pharmaceutical composition according to claim 23 in the form of an oral dosage unit containing about 1–200 mg of the compound.

25. A method of treating a central nervous system ailment related to the glycine binding site on the NMDA receptor complex comprising administering to a subject in need thereof an effective amount of a compound of formula I or a tautomeric form thereof selected from the group consisting of

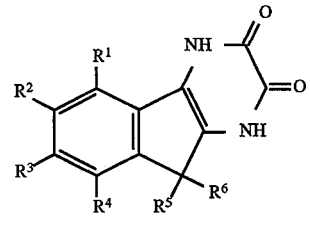

or

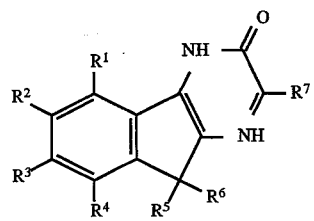

wherein $R^1$, $R^2$, $R^3$ and $R^4$ independently are hydrogen, halogen, $C_{1-6}$-alkyl or $C_{1-6}$-alkoxy;

$R^5$ is hydrogen; hydroxy; halogen; cyano; $C_{1-6}$-alkyl optionally substituted with hydroxy; $C_{1-6}$-alkoxy optionally substituted with one or two phenyl group(s) wherein said phenyl group(s) is/are optionally substituted with halogen; $C_{1-6}$-(alkoxyalkoxy); $C_{1-6}$-thioalkyl optionally substituted with an amino group wherein said amino group is optionally mono or disubstituted with $C_{1-6}$-alkyl; $C_{1-6}$-acyloxy; phosphono; $C_{1-6}$-alkoxy disubstituted phosphonyl;, or a morpholina or piperazinyl group which is optionally substituted with a $C_{1-6}$-alkyl group wherein said alkyl group is optionally substituted by hydroxy or wherein the morpholina or piperazinyl group is optionally substituted with one or two phenyl group(s) wherein said phenyl group(s) is/are optionally substituted with methoxy; and $R^6$ is hydrogen, $C_{1-6}$-alkyl or phenyl; or $R^5$ and $R^6$ together represent a carbonyl group, a hydroxyimino group or a benzyloxyimino group; and $R^7$ is hydrogen, phenyl or —$CH_2OR^8$ wherein $R^8$ is hydrogen or benzyl; or a pharmaceutically acceptable salt thereof.

26. A compound which is:

9-Hydroxyimino-9H-indeno[1,2-b]pyrazin-3(4H)-one;

9-Chloro-9H-indeno[1,2-b]pyrazine-3(4H)-one;

9-Hydroxy-9H-indeno[1,2-b]pyrazine-3(4H)- one;

9-Hydroxy-9-phenyl-9H-indeno[1,2-b]pyrazine-3(4H)-one;

9-Acetoxy-9-phenyl-9H-indeno[1,2-b]pyrazine-3(4H)-one; or a pharmaceutically acceptable salt thereof.

27. A pharmaceutical composition comprising a compound according to claim 26 together with a pharmaceutically acceptable carrier or diluent.

28. The pharmaceutical composition according to claim 27 in the form of an oral dosage unit or parenteral dosage unit.

29. The pharmaceutical composition according to claim 28 in the form of an oral dosage unit containing about 1–200 mg of the compound.

* * * * *